(12) United States Patent
Verness

(10) Patent No.: US 7,065,411 B2
(45) Date of Patent: Jun. 20, 2006

(54) ELECTRICAL MEDICAL LEADS EMPLOYING CONDUCTIVE AEROGEL

(75) Inventor: David D. Verness, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 583 days.

(21) Appl. No.: 10/421,455

(22) Filed: Apr. 23, 2003

(65) Prior Publication Data

US 2004/0215300 A1 Oct. 28, 2004

(51) Int. Cl.
*A61N 1/05* (2006.01)
*A61N 1/04* (2006.01)

(52) U.S. Cl. .................. 607/116; 607/115; 607/119; 607/122

(58) Field of Classification Search ............... 607/115, 607/116, 119, 121–123; 600/372–374, 377, 600/397
See application file for complete search history.

(56) References Cited

U.S. PATENT DOCUMENTS

| | | | |
|---|---|---|---|
| 3,333,045 A | 7/1967 | Fisher et al. | 174/20 |
| 3,348,548 A | 10/1967 | Chardack | 128/418 |
| 3,924,639 A | 12/1975 | Hess | 128/418 |
| 4,033,355 A | 7/1977 | Amundson | 128/404 |
| 5,007,435 A | 4/1991 | Doan et al. | 128/784 |
| 5,246,014 A | 9/1993 | Williams et al. | 607/122 |
| 5,545,203 A | 8/1996 | Doan | 607/122 |
| 5,584,873 A | 12/1996 | Shoberg et al. | 607/122 |
| 5,649,967 A * | 7/1997 | De Bellis et al. | 607/9 |
| 5,760,341 A | 6/1998 | Laske et al. | 174/126.2 |
| 5,796,044 A | 8/1998 | Cobian et al. | 174/103 |
| 6,018,683 A | 1/2000 | Verness et al. | 607/122 |
| 6,052,625 A | 4/2000 | Marshall | 607/122 |
| 6,061,598 A | 5/2000 | Verness et al. | 607/122 |
| 6,119,042 A | 9/2000 | Verness et al. | 607/122 |
| 6,285,910 B1 | 9/2001 | Verness et al. | 607/122 |

FOREIGN PATENT DOCUMENTS

WO    WO 95/01165    1/1995

OTHER PUBLICATIONS

Kay, Liz F., "Space Fills Void Aerogel Created," *Los Angeles Times*, Science File, p. A14 (Jun. 10, 2002).
Labrador, A.W. et al., "Silica Aerogel Cherenkov Counters for the Isotope Matter Antimatter Experiment," *IMAX-ICRC*, http://www.srl.caltech.edu/personnel/labrador/icrc93_aero.htm, p. 1-5 (1993).
Rolison, D.R. et al., "Electrically Conductive Oxide Aerogels: New Materials in Electrochemistry," *J. Mater. Chem.*, vol. 11, p. 963-80 (2001).

* cited by examiner (Continued)

Primary Examiner—Robert E. Pezzuto
Assistant Examiner—Yun H. Lee
(74) *Attorney, Agent, or Firm*—Michael C. Soldner; Girma Wolde-Michael

(57) ABSTRACT

Conductive aerogels are employed in fabrication of electrical medical leads adapted to be implanted in the body and subjected to bending stresses. An elongated, flexible and resilient, lead body extends from a proximal end to a distal end and includes an insulative sheath having an elongated lumen through which an elongated conductor extends. A layer of conductive aerogel is disposed over the conductor deforming upon movement of the conductor within the lumen against the aerogel in response to applied stresses.

15 Claims, 4 Drawing Sheets

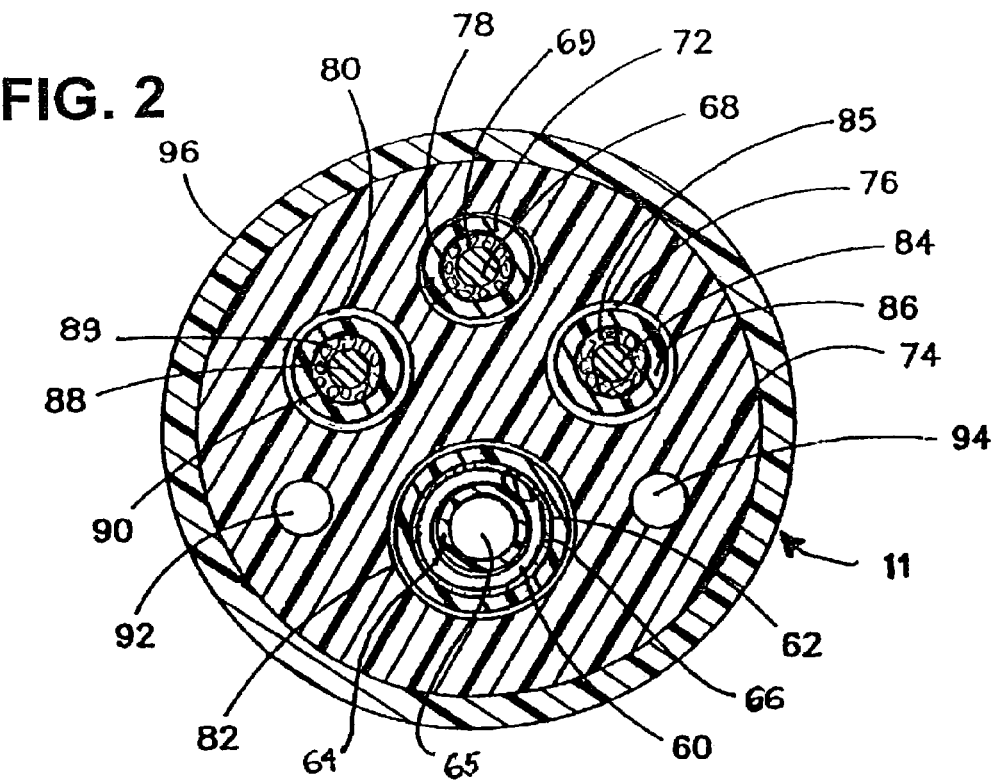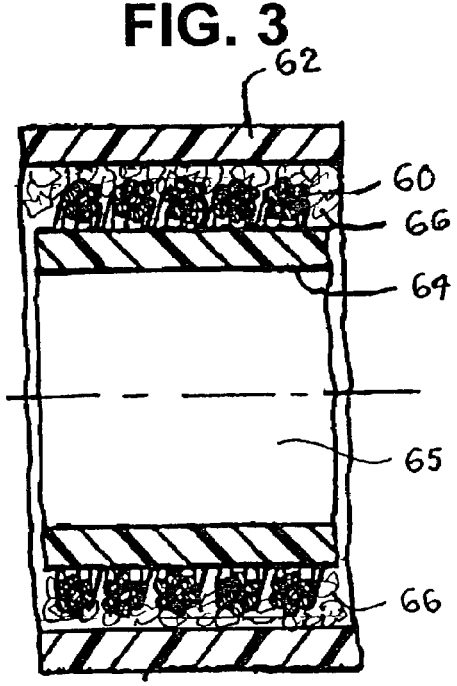

ELECTRICAL MEDICAL LEADS EMPLOYING CONDUCTIVE AEROGEL

FIELD OF THE INVENTION

The present invention relates to implantable medical devices (IMDs) intended for chronic implantation in the body and particularly to electrical medical leads for applying electrical stimulation to and/or sensing electrical activity of the body, particularly cardiac leads for applying electrical stimulation to and/or sensing electrical activity of the heart at one or more electrode positioned at a cardiac implantation site within a heart chamber or cardiac vessel adjacent a heart chamber.

BACKGROUND OF THE INVENTION

Implantable medical electrical stimulation and/or sensing leads intended for chronic implantation in the body are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, endocardial leads are placed through a transvenous route to locate one or more sensing and/or stimulation electrode along or at the distal end of the lead in a desired location in a chamber of the heart or a blood vessel of the heart. In order to achieve reliable sensing of the cardiac electrogram and/or to apply stimulation that effectively paces or cardioverts the heart chamber, it is necessary to accurately position the electrode surface against the endocardium or within the myocardium at the desired site and fix it during an acute post-operative phase until fibrous tissue growth occurs.

The pacemaker or implantable cardioverter/defibrillator (ICD) implantable pulse generator (IPG) or the monitor is typically coupled to the heart through one or more of such endocardial leads having a lead body extending between a proximal lead connector assembly and distal electrode. The proximal lead connector assembly comprising one or more connector element is connected with a connector header of the IPG or monitor. The lead body typically comprises one or more insulated conductive wire surrounded by an insulating outer sleeve. Each conductive wire couples a proximal lead connector element with a distal stimulation and/or sensing electrode. An endocardial cardiac lead having a single stimulation and/or sensing electrode at the lead distal end and a single conductive wire is referred to as a unipolar lead. An endocardial cardiac lead having two or more stimulation and/or sensing electrodes at the lead distal end and two or more conductive wires is referred to as a bipolar lead or a multi-polar lead, respectively.

In order to implant an endocardial lead within a heart chamber, a transvenous approach is utilized wherein the lead is inserted into and passed through the sub-clavian, jugular, or cephalic vein and through the superior vena cava into the right atrium or ventricle as depicted, for example, in U.S. Pat. No. 5,545,203. An active or passive fixation mechanism is incorporated into the distal end of the endocardial lead and deployed to maintain the distal end electrode in contact with the endocardium or within the myocardium at the implantation site. An introduction mechanism, e.g., a stiffening stylet and/or a guide catheter, is employed to advance the distal electrode(s) to the electrode implantation site(s).

More recently, endocardial pacing and cardioversion/defibrillation leads have been developed that are adapted to be advanced using particular guide mechanisms into the coronary sinus and coronary veins branching therefrom in order to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at a desired site although active fixation mechanisms, e.g., minute helixes that are screwed into the vessel wall, can be employed.

The heart beats approximately 100,000 times per day or over 30 million times a year, and each beat stresses the lead conductors and insulation. Over the years of implantation, the lead conductors and insulation are subjected to cumulative mechanical stresses as well as material reactions that can result in degradation of the insulation or fractures of the lead conductors with untoward effects on IMD performance and patient well-being. The endocardial lead bodies of pacing and ICD leads are subjected to continuous stretching and flexing as the heart contracts and relaxes and are formed to be highly flexible, resilient, and durable employing durable bio-compatible lead conductor and insulator materials and structures.

Initially developed chronically implanted unipolar and bipolar cardiac pacing leads employed flexible silicone rubber tube having a single lumen and two lumens, respectively in which single filar wire conductors formed of stainless steel and later of MP35N alloy that were wound into wire coils were inserted and electrically coupled to a proximal lead connector element and a distal pace/sense electrode. Early implantable, endocardial and epicardial, bipolar cardiac pacing leads of the type disclosed in U.S. Pat. No. 3,348,548, that were clinically implanted in the 1960s, had two lumens arranged side-by-side and coiled wire conductors disposed in each lumen. The wire coil and silicone rubber tube of such endocardial pacing leads allow the lead body to stretch axially and provide a coil lumen for receiving a stiffening stylet during transvenous lead advancement.

Such lead bodies fabricated at that time were relatively large in diameter, and the side-by-side arrangement was believed to be responsible for lead body fractures. In addition, effective passive and active distal fixation mechanisms were not available, and displacement of the distal electrodes were common occurrences. Surgeons resorted to stiffening the lead body by leaving the stylet in place to prevent dislodgement, but the stiffening stylet then often fractured within the wire coil lumen, and the sharp broken stylet ends initiated a lead fracture. Moreover, a portion of the lead body was (and is to the present time) often implanted between the first rib and right clavicle as illustrated in the above-referenced '545 patent, and the stresses on the lead body caused the relatively large diameter lead insulator and body to be crushed and fracture.

A great deal of effort has been undertaken over the years to reduce these complications by developing fracture and crush resistant lead bodies and to provide the above-mentioned active and passive fixation mechanisms that effectively reduced lead dislodgement. At the same time, many other material and structural improvements have been made in lead conductors, lead insulators, electrodes, and various other electrical medical lead components to reduce the lead body diameter and increase its lubricity, to increase conductivity of the lead conductor, to increase the number of lead-borne electrodes, to decrease stimulation thresholds, particularly cardioversion/defibrillation and pacing thresholds, and optimize sensing of the electrogram, to reduce inflammation at the electrode-tissue interface, to optimize electrode shapes and materials, to incorporate sensors in some instances, and to otherwise simplify implantation, reduce complications, assure reliable pacing and cardioversion/defibrillation, and increase the implantation lifetime of such cardiac leads and other electrical medical leads. In particular, many changes have been made in the materials used in and the fabrication of lead bodies extending between the proximal lead connector assembly and distal electrodes(s) and sensor(s).

Most current endocardial cardiac leads employ multi-filar, parallel-wound, coiled wire conductors electrically connected in common in an electrically redundant fashion as a single polarity lead conductor in each of the unipolar, bipolar and multi-polar lead configurations. Such redundant coiled wire conductors of bipolar and multi-polar lead bodies are coaxially arranged about the stiffening stylet receiving lumen and insulated from one another by coaxially arranged insulating sheaths separating each coiled wire conductor from the adjacent coiled wire conductor(s). The number of separate lead conductors that can be incorporated in a lead body of a given diameter is limited in this coaxial winding approach.

In certain cases, the need for increased numbers of lead conductors in the lead body has led to the development of separately insulated, coiled wire conductors that are parallel-wound with a common diameter and are separately coupled between a proximal connector element and to a distal electrode or terminal in the manner described in commonly assigned U.S. Pat. No. 5,007,435, for example. The coaxial construction technique may also be combined with the parallel-winding technique to multiply the total number of separate coiled wire conductors accommodated within a specified endocardial lead body outer diameter.

Improvements in stranded wire conductors and lead body materials have more recently led to the combination of substantially straight, stranded wire conductors and at least one coiled wire conductor providing a stylet lumen as illustrated in commonly assigned U.S. Pat. Nos. 5,584,873, 6,052,625, and 6,285,910, for example. In these lead bodies, ETFE sleeve insulators encase the stranded wire conductors, and a PTFE sleeve insulator surrounds the multi-filar, coiled wire, conductor. The insulated wire conductors are received in lumens of an elongated lead body insulator that also incorporates elongated, empty, compression lumens.

Typically, the lumens in lead body insulators receiving substantially straight, stranded wire conductors or coiled wire conductors are not otherwise filled with a filler or the like. However, the above-referenced '203 patent discloses coaxial lead bodies of the types disclosed above as well as a lead body incorporating multiple, coiled wire conductors arranged side-by-side within lumens of the lead body insulator. The lumens are also reinforced against crushing with a liquid polymer, e.g., Silastic® silicone rubber, silicone rubber adhesive or polyurethane, that solidifies in place. However, encasing the turns of the coiled wire conductors along the length of the lead body with such materials can stiffen the lead body unduly and may increase the likelihood of stress-related fracture at other points along the lead body.

To some extent, it has been recognized that the relative movement of lead conductors with respect to the surrounding wall of silicone rubber tube can abrade the conductors or tube, perhaps due to the abrasive action of silica of the silicone rubber compound, and cause the lead body to fail. In commonly assigned U.S. Pat. No. 5,796,044, coiled wire, single filar and multi-filar, conductors are disclosed that are sheathed loosely within a separate, coiled, insulating sheath allowing a gap or space to be present between the exterior surface of the coiled wire conductor and the adjacent interior surface of the insulating sheath. The insulating sheath is loosely fitted around the coiled wire conductor to avoid concentrating corrosion effects at the site of a defect, allowing any corrosion that may occur as a result of the defect to be spread over a larger wire surface. The coiled insulating sheath is preferably included within the lumen of a non-coiled outer insulating sheath.

It is suggested in U.S. Pat. No. 3,333,045 that the tube lumen be backfilled with a liquid silicone fluid or powdered ETFE to lubricate the surfaces of the lumens of silicone rubber tube receiving stranded, drawn-brazed stranded (DBS) wires, loosely coiled into coiled wire conductors. Incorporating such non-conductive lubricating or reinforcing materials within the conductor lumen of a lead body insulator may or may not reduce the possibility of lead conductor fracture through abrasion or crushing. The electrical connection between the distal electrode or sensor and the proximal lead connector element is interrupted if a fracture of the lead conductor does occur with or without the lubricating or reinforcing materials within the lead conductor lumen.

It has been proposed to include other materials or mechanisms to provide a form of redundancy with the coiled or straight stranded wire conductor to compensate for a complete fracture or the reduced conductivity attendant to a partial fracture of the conductor. In U.S. Pat. No. 4,033,355, the coiled wire conductor is tightly fitted within a conductive silicone rubber tube, e.g., silicone rubber compounded with conductive particles, e.g., carbon. The tight fitting is determined to be necessary to ensure that the wire coil turns make intimate contact with the conductive silicone rubber so that a section of conductive silicone rubber bridges any fractured ends of the wire conductor. An internal block of conductive silicone rubber surrounding a section of the coiled wire conductor within the lead connector assembly of the cardiac pacing lead disclosed in U.S. Pat. No. 3,924,639 is provided to make a temporary electrical connection with the lead conductor. The use of conductive silicone rubber as disclosed in the '355 patent raises the same issues of reduced lead body flexibility and abrasion possibly increasing the risk of fracture as the use of the tight fitting electrically insulating silicone rubber disclosed in the above-referenced '203 patent. While such silicone rubber materials can be made conductive by incorporating suspended conductive particles to a certain degree, but the conductivity does not match that of the lead conductor itself.

Endocardial leads that have an increased resistance to fracture and the capability of continued function after fracture of a lead conductor are disclosed in commonly assigned U.S. Pat. Nos. 6,018,683, 6,061,598, 6,119,042 and 6,285,910 and in the above-referenced '044 patent. The endocardial leads are provided with a monofilar or multi-filar coiled wire conductor that extends along the length of the lead body between a proximal electrical connector element and a distal electrode in a conventional manner. In addition, a stranded wire conductor extends loosely along the coiled wire conductor from a point along the lead body located proximal to the point of expected breakage of the coiled wire conductor to a point along the lead body located distal to the point of expected breakage. In certain embodiments, the proximal and distal ends of the stranded wire conductor are electrically and mechanically coupled to the coiled wire conductor, limiting the extensibility of the coiled wire conductor, rendering the coiled wire conductor less susceptible to axially applied tensile forces, and also providing for continued electrical connection between the connector element and the electrode in the event that the coiled wire conductor fractures intermediate the proximal and distal ends of the stranded wire conductor. In other embodiments, the stranded wire conductor is coupled only at its proximal or distal end to the coiled wire conductor or may simply be located in the same lumen as the coiled wire conductor without mechanical connection to the coiled conductor. Due to the confines of the lumen, the stranded and coiled wire conductors come into contact at numerous points along their respective lengths so that a mechanical connection is not necessary.

The fabrication of electrical medical lead bodies often requires directing lead conductors through cavities in the lead body insulator other than conductor lumens per se in order to make electrical connections to lead connector elements or distal electrodes or sensors. For example, the lead body insulator of the endocardial leads disclosed in the above referenced '625, '873, '683, '598, '042 and '910 incorporate bifurcation sleeves or trifurcation sleeves in order to connect two or three, respectively, connector assemblies to selected lead conductors that are diverted through branch sleeve cavities or lumens. These sleeve lumens are typically backfilled with liquid silicone rubber adhesive that solidifies within the cavity about the short segments of conductor wire traversing the cavity and immobilizes them. At times, the immobilization of the lead conductor segment can cause or does not prevent the lead conductor traversing the sleeve lumen to fracture due to chronically applied stress.

It is therefore desirable to provide a relatively simple, electrically redundant, bridging of a fractured wire conductor traversing a cavity, lumen or other space of the lead body.

BRIEF SUMMARY OF THE INVENTION

In accordance with one aspect of the present invention, cavities, lumens or other spaces (herein referred to collectively as lumens) of a cardiac lead body adjacent to a lead conductor are filled with a solid rigid electrically conductive foam, particularly a conductive aerogel, that presents a "deformable space" to the lead conductor traversing the lumen.

The solid rigid, conductive aerogel foam is in intimate contact with the un-insulated surface of the lead conductor providing a redundant conductive path alongside the conductor. A fracture of the lead conductor section that increases conductor resistance or results in an open circuit is bridged by a continuous segment of the conductive aerogel that the lead conductor contacts.

In fabrication, the lead conductor is preferably coated with a fluid conductive aerogel that solidifies about the lead conductor between the lead conductor and an insulating tube, sheath or layer surrounding the lead conductor.

The solidified conductive aerogel is relatively rigid but can be stretched, crushed, or deformed when a sufficient force is applied. During chronic implantation, the solidified, conductive, aerogel is stretched, compressed or deformed by flexing of the lead conductor within the lead body insulator due to externally applied stresses, whereby the lead conductor is allowed to flex within the space created by the deformation thereby releasing stress on the lead conductor. The solidified conductive aerogel is also deformed if a crushing force is applied to the lead body. The deformation crushes the conductive aerogel upon itself to the extent that the lead conductor is bent or crushed but the conductive aerogel does not itself fracture and makes contact with the lead conductor to bridge any lead conductor fracture due to crushing or severe bending. The crushed conductive aerogel retains its conductivity providing a conductive bridge across any lead conductor fracture.

Conductive or non-conductive aerogels can be employed to fill spaces in other IMDs where it would be desirable to restrict motion of conductors or other components disposed within the space that would lead to fracture or failure over prolonged exposure to applied stresses.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 2 is an end cross-section taken along lines 2—2 of FIG. 1 illustrating a first aspect of a first embodiment of the present invention;

FIG. 3 is a side cross-section view of a sub-assembly of FIG. 2 of a coiled wire conductor coated with a conductive aerogel layer disposed between inner and outer non-conductive tubes;

FIG. 4 is an end cross-section view of the sub-assembly of FIG. 2 of a stranded wire cable conductor coated with a conductive aerogel layer disposed within a non-conductive layer or tube;

DETAILED DESCRIPTION OF THE INVENTION

Figure 1:
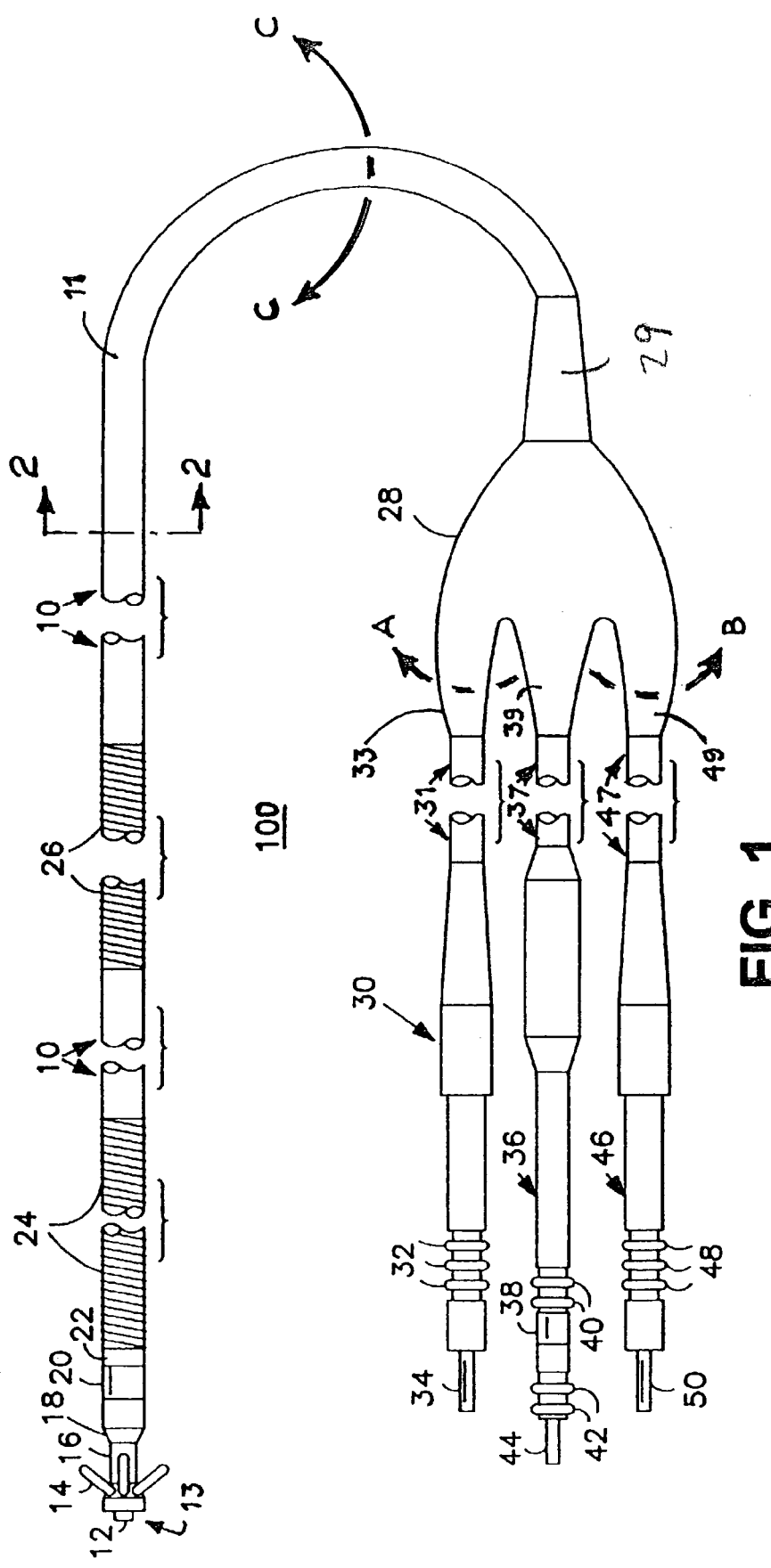
FIG. 1 is a conventional ICD lead having a trifurcation in the lead body in which the present invention may be advantageously practiced.

In the following detailed description, references are made to illustrative embodiments of methods and apparatus for carrying out the invention. It is understood that other embodiments can be utilized without departing from the scope of the invention.

In accordance with the present invention, conductive aerogels are incorporated into IMDs and preferred embodiments incorporating conductive aerogels into implantable medical lead bodies are described herein. As characterized by D. R. Rolison et al., "Aerogels . . . are nanoscale mesoporous materials of low density and high surface area . . . in which nano-meter solid domains (the "being") are networked through a continuous highly porous volume of free space (the "nothingness") . . ." (see "Electrically conductive oxide aerogels: new materials in electrochemistry", *J. Mater. Chem.*, 2001, 11:963–80). A typical aerogel is 99.8% air (nothingness) and 0.2% matter (being) and is the lightest known material weighing about 3 milligrams per cubic centimeter and one of the best known thermal insulators. Aerogel is sometimes called "solid smoke" because of its extraordinarily low density and the bluish cast it takes when light shines on it.

The first non-conductive aerogels were created in the 1930s of silicon dioxide and have largely remained a scientific curiosity, but various potential uses of non-conductive and more recently developed conductive aerogels are outlined in the Rolison et al. article, including use as insulators, sensor elements, Cerenkov detectors, in Space Shuttle missions and in the "Stardust" mission launched Feb. 7, 1999, to intercept the tail of comet Wild-2 in 2004, capture samples of the comet's tail and return to earth with the samples.

The Rolison article describes a variety of conductive aerogels, including the early-developed aerogels rendered conductive by incorporating carbon soot into the "being" or incorporating various metal oxides into the "being". Preferred conductive aerogels can be formed incorporating platinum and gold particles or various metal oxides within the aerogel. Aerogels are produced from certain gels described in the Rolison article, for example, by heating the gel under pressure, which causes the liquid in the gel to become supercritical (in a state between a liquid and a gas) and lose its surface tension. In this state, the liquid may be removed from the gel by applying additional heat, without disrupting the porous network formed by the gel's solid component. Exemplary methods of fabricating and potential uses of the conductive metal oxide aerogels in electrochemical cells, capacitors, catalytic converters, and the like are described in the Rolison article.

It is my belief that such aerogels, particularly conductive aerogels, can be advantageously used in many IMD applications. Particular exemplary uses in the context of an electrical medical lead having a flexible and resilient lead body that is likely to be subjected to bending and compression stresses when implanted in the body are described as follows.

In fabrication, one or more lead conductor is extended through a conductor lumen, and a mass of fluid conductive aerogel is deposited within at least a portion of and extending for a distance along the elongated lumen in contact with the conductor. The deposition is preferably effected by coating the surface of the conductor with a fluid conductive aerogel before the aerogel coated conductor is covered by an insulating sheath or fitted into a lumen of an insulating tube or tube. The coating can be formed by extrusion of the fluid conductive aerogel over a continuous length of the conductor. The fluid conductive aerogel solidifies in intimate contact with the conductor to provide a generally rigid support of the lead conductor and a deformable space thereover.

The solidified conductive aerogel is relatively rigid but can be crushed or deformed or stretched axially when a sufficient force is applied. Thus, the conductive aerogel becomes a deformed space. Preferably, one or more further non-conductive polymer layers can be extruded over the conductive aerogel layer.

It will be understood that the present invention can be practiced in the context of any electrical medical lead, e.g., any conventional cardiac pacing leads, ICD leads, neurostimulation leads, etc., and that the figure merely illustrate one exemplary electrical medical lead. FIG. 1 therefore illustrates an exemplary endocardial lead 100, embodied as a transvenous ICD lead of the type disclosed in the above-referenced '625 patent, in which the present invention is advantageously practiced. The lead 100 comprises an elongated lead body 10 extending between proximal lead connector assemblies 30, 36 and 46 and a lead body distal end 13. The lead body 10 is a complex structure having distinct proximal, intermediate, and distal regions through which four electrical lead conductors that are electrically insulated from one another by components of a lead body insulator extend.

The distal region of the lead 100 includes a number of components, in this embodiment, including an elongated, open-coil, proximal cardioversion/defibrillation electrode 26, an elongated open-coil, distal cardioversion/defibrillation electrode 24 and a distal tip-ring assembly. The elongated open-coil structure retains flexibility in along the lengths of the proximal and distal cardioversion/defibrillation electrodes 26 and 24. The distal tip-ring assembly includes distal tip pace/sense electrode 12, tine sheath 16 carrying tines 14, tip-ring spacer component 18, ring-shaped pace/sense electrode 20, and ring-coil spacer component 22. The tine sleeve 16 fabricated of silicone rubber or a relatively softer polyurethane, and the tip-ring and ring-tip spacers 18 and 22 fabricated of relatively harder plastics, for example polyurethane having a Shore hardness of at least 75D, to provide a relatively rigid distal tip-ring assembly extending to the distal end of distal defibrillation.

The lead body insulator in the intermediate region comprises an elongated tubular lead body insulator 11, depicted in cross-section in FIG. 2. The lead body insulator 11 in the proximal region comprises a trifurcation sleeve 28 depicted in FIG. 3, joining the proximal end of the elongated tubular lead body insulator 11 with the distal ends of insulating sleeves 31, 37 and 47 extending proximally from the trifurcation sleeve 28 to the proximal lead connector assemblies 30, 36, and 46, respectively. The trifurcation sleeve 28 includes an axially extending sleeve trunk 29 and trifurcation branches 33, 39 and 49. Each of the sleeve trunk 29 and trifurcation branches 33, 39 and 49 encloses a sleeve cavity or lumen that proximal segments of lead conductors extend through. The trifurcation branches 33, 39 and 49 can be unintentionally stressed in movement outward in the directions of arrows A and B, respectively, during handling at implantation or chronically due to body motion.

The lead body insulator 11 in the distal region is preferably fabricated of polyurethane and supports various insulating components and spacers supporting the distal array of components, e.g., electrodes 12, 20, 24 and 26 and the distal passive fixation tine sheath 16 as disclosed in detail in the above-referenced '625 patent. The lead body 10 comprises four mutually insulated, elongated conductors disposed within the lead body insulator 11 that are not visible in FIG. 1. Three of the insulated conductors are stranded wire conductors, each coupled to one of ring-shaped pace/sense electrode 20, elongated wire coil, distal cardioversion/defibrillation electrode 24 and elongated wire coil, proximal cardioversion/defibrillation electrode 26. A fourth, wire coil, conductor is coupled to distal tip pace/sense electrode 12.

Connector assembly 30 supports a single connector pin 34, coupled to the conductor coupled to the distal cardioversion/defibrillation electrode 24, and is provided with sealing rings 32 to seal the connector assembly 30 within the connector bore of an ICD IPG connector header upon implantation. Similarly, connector assembly 46 is provided with a single connector pin 50 coupled to the conductor coupled to the proximal cardioversion/defibrillation electrode 26, and is provided with sealing rings 48 to seal the connector assembly 46 within a further connector bore of an ICD IPG connector header upon implantation. Connector assembly 36 takes the form of an IS-1 type connector assembly provided with a connector pin 44 coupled to the coiled conductor extending to tip pace/sense electrode 12 and a connector ring 38 coupled to a cabled conductor extending to ring-shaped pace/sense electrode 20. Sealing rings 40 and 42 provide a seal between connector pin 44 and connector ring 38 and seal the connector assembly 36 within the connector bore of the ICD IPG connector block upon implantation.

As shown in FIG. 2, the lead body insulator 11 that extends from the trifurcation sleeve 28 to the tip-ring assembly at the distal end of the lead is preferably formed of an extruded multi-lumen tube 74 surrounded by an overlay tube or sleeve 96. The multi-lumen tube 74 and sleeve 96 are fabricated of materials, e.g., extruded silicone rubber or polyurethane having a Shore hardness of 80A or 90A, or the like. The multi-lumen tube 74 is formed with conductor lumens 76, 78, 80, and 82 and stress or compression lumens 92 and 94 that are located diametrically opposite lumens 80 and 76. The compression lumens 92 and 94 are intended to relieve bending stresses and resist crushing forces as described in the above-referenced '873 patent. The sleeve 96 has approximately the same outer diameter and the same thickness as the wire from which the elongated wire coil cardioversion/defibrillation electrodes 24 and 26 are fabricated to make the elongated lead body 11 isodiametric between the lead body distal end and the trifurcation sleeve 28.

In the preferred embodiment, a coiled wire conductor 60 extends through a lumen 82 between distal tip pace/sense electrode 12 and connector pin 44 via trifurcation sleeve 28 and insulating sleeve 37. Stranded wire cable conductors 84 and 88 extend through respective lumens 76 and 80 between the respective proximal and distal coil cardioversion/defibrillation electrodes 24 and 26 and respective connector pins 34 and 50 via trifurcation sleeve 28 and respective insulating sleeves 31 and 47. A further stranded wire cable conductor 68 extends through a fourth lumen 78 between the ring-shaped pace/sense electrode 20 and connector ring 38 via trifurcation sleeve 28 and insulating sleeve 37.

Despite the care taken in design and fabrication, there remains a risk of damage to lead conductors 60, 68, 84 and 88 within the respective lumens 82, 78, 82 and 80 as the lead body 10 is flexed repeatedly as in the direction C—C depicted in FIG. 1. Consequently, in one aspect of the present invention, a conductive aerogel is introduced over the outer surfaces of the lead conductors 60, 68, 84 and 88. A thin layer or coating of liquid conductive aerogel can be applied by spraying, dipping, painting, or extrusion over the conductor, and the conductive aerogel coating can then be dried. The conductive aerogel layer or coating can advantageously penetrate between wire strands and between the turns of the coiled wire conductor 60. The inner tube 64 can first be inserted into the conductor lumen 82 to maintain it open during application of the conductive aerogel coating. Then, the conductive aerogel coated lead conductor 60 is inserted into the lumen of the tube 62. Similarly, the conductive aerogel coated stranded wire cable conductors 68, 84 and 88 are coated with the respective insulating layers 72, 86 and 90.

The solidified conductive aerogel coatings fill an elongated cavity or space surround the outer surfaces of the stranded wire conductors 68, 84, and 88 within the insulating layers 72, 86 and 90. Solidified conductive aerogel also coats the coiled wire conductor 60 within the lumen of tube 62. The solidified conductive aerogel also extends along the lengths of the respective lumens 76, 78, 80, and 82 and is deformed if sufficient force is applied to the lead body 10. The deformation crushes the solidified conductive aerogel upon itself to the extent that the lead conductors are bent or crushed. The crushed mass of conductive aerogel does not itself fracture and makes contact with the lead conductors to bridge any lead conductor fractures due to crushing or severe bending. The crushed conductive aerogel retains its conductivity providing a conductive bridge across any lead conductor fractures.

Referring to FIGS. 2 and 3, an inner PTFE tube 64 having an inner tube lumen 65 is inserted into the lumen of the coiled wire conductor 60, and the coiled wire conductor 60 is encased within the lumen of an outer PTFE tube 62. The coiled wire conductor 60 is coated with a thin conductive aerogel coating or layer 66 prior to insertion of the coiled wire conductor 60 and inner PTFE tube 64 into the lumen of the outer PTFE tube 62. The assembly of inner PTFE tube 64, the conductive aerogel coated coiled wire conductor 60, and the outer PTFE tube 62 is fitted within the lumen 82 of elongated lead body 11 before the conductor ends are coupled to the distal tip electrode 12 and proximal connector pin 44 via trifurcation sleeve 28 and insulating sleeve 37.

Referring to FIGS. 2 and 4, the stranded wire cable conductors 84 and 88 are coated with thin conductive aerogel layers 85 and 89, respectively, and then over coated with thin ETFE sheaths or layers 86 and 90, respectively. The coated stranded wire cable conductors 84 and 88 are inserted into respective lumens 76 and 80 and coupled to the respective proximal and distal coil cardioversion/defibrillation electrodes 24 and 26 and respective connector pins 34 and 50 via trifurcation sleeve 28 and respective insulating sleeves 31 and 47. The further stranded wire cable conductor 68 is also coated with a thin conductive aerogel layer 69 and then over coated with an ETFE or PTFE sheath or layer 72 before being extended through fourth lumen 78 and coupled to the ring-shaped pace/sense electrode 20 and connector ring 38 via trifurcation sleeve 28 and insulating sleeve 37. The insulating sheaths or layers 72, 86, 90 may be formed of a wide variety of biocompatible, biostable, non-conductive polymer materials including the aforementioned PTFE and ETFE, as well as other fluoropolymers, e.g., tetrafluoroethylene-hexafluoropropylene-vinylidene fluoride (THV), fluorinated ethylene propylene (FE P), polyfluoroalkoxyl (PFA), polychlorotrifluoroethylene (PCTFE), polyvinylidene fluoride (PVDF), and high durometer polyurethanes, e.g., Pellethane 75D and Tecothane 75D, etc.

The application of insulating sheaths or the formation of insulating layers 72, 86, 90 over the aerogel layers 69, 85, and 89, respectively, effectively creates sheath or layer lumens filled with the aerogel layers 69, 85, and 89 and the stranded wire cable conductors 68, 84, and 88, respectively.

The coiled wire conductor 60 can be formed of a single coiled wire or can be formed of multi-filar stranded cable conductor wound into a coil, e.g., the seven wire strands as shown, for example, in greater detail in FIG. 3. In either case, the coiled wire conductor can comprise a plurality, e.g., four, of such single coiled wires or stranded coiled wires that are wound having a common diameter as shown in FIG. 3.

The stranded wire cable conductors 68, 84, and 88 shown in greater detail in FIG. 4 can take any of the forms disclosed in U.S. Pat. Nos. 5,760,341 and 5,246,014 and in the above-referenced '873 patent. The number and fabrication of the individual strands of the stranded wire cable conductors 68, 84, and 88 may vary as a function of the expected level of current to be carried by the conductors and as a function of the material of which they are fabricated. The stranded wire cable conductors 68, 84 and 88 can be fabricated in any of the known types, e.g., 1×7 strand cables or the depicted 7×7 strand cables, for example. Typically, single filar coiled wire conductors and strands or stranded cable wire conductors would be fabricated of MP35N alloy wire or silver core MP35N wire strands to provide increased conductivity. MP35N alloy or surgical grade stainless steel or the like encases the silver core in a drawn brazed stranded (DBS) fabrication process or a drawn filled tube (DFT) fabrication process well known in the art. The invention may be practiced employing wire cross-section and corresponding coiled insulating sheath cross-section shapes differing form the depicted circular shapes, e.g. elliptical or rectangular shapes.

The outer diameters of the insulating layers 72, 86 and 90 and tube 62 are smaller than the diameters of the respective lumens 76, 78, 80, and 82, respectively to facilitate assembly. It will be understood that the relative thicknesses of the ETFE or PTFE layer 72, the ETFE layers 86 and 90, and the tube 62 to the diameters of the lead conductors 68, 84, 86 and 60, respectively, that they encase or surround are exaggerated for ease of illustration in the drawing figures.

Figure 5:
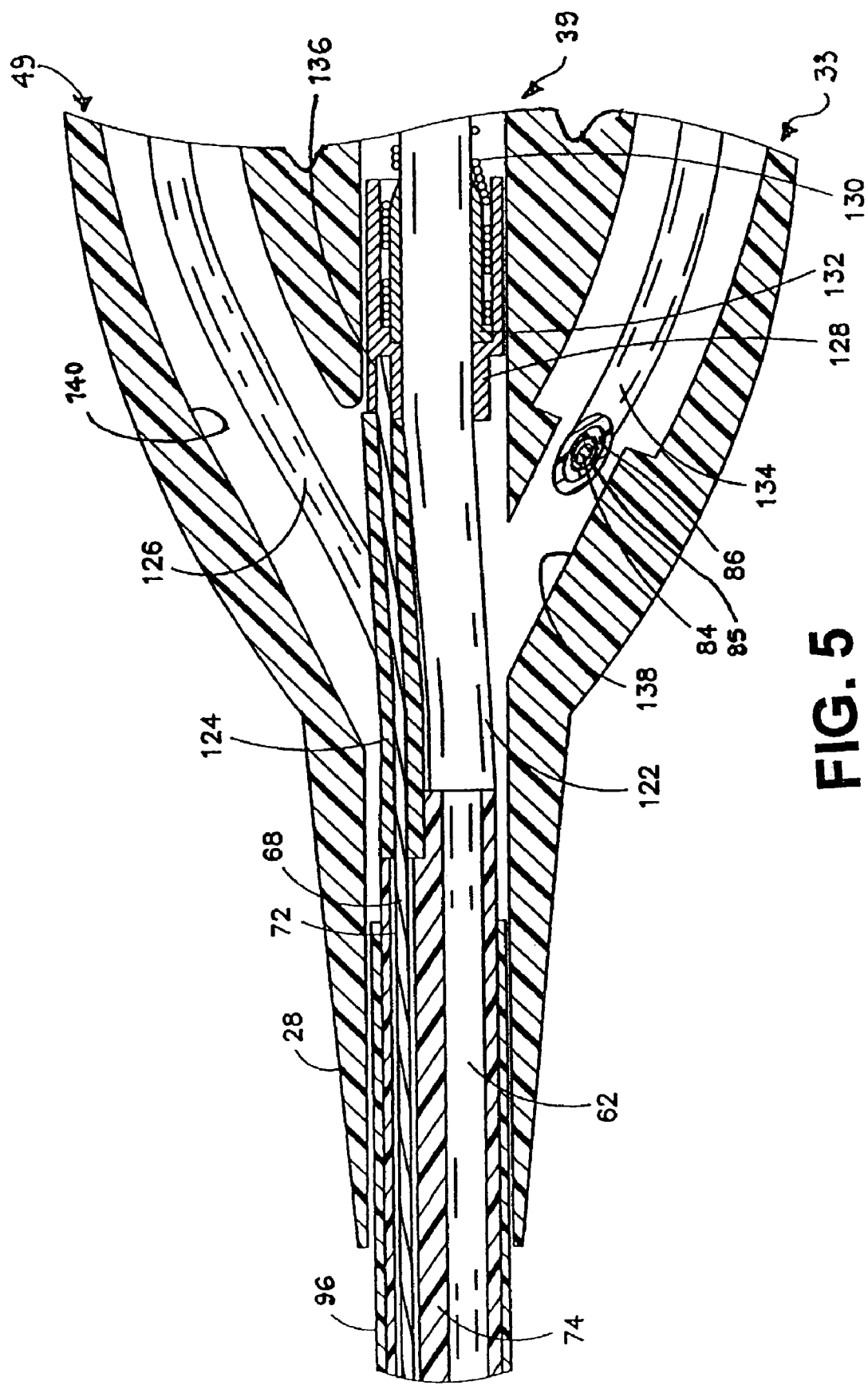
FIG. 5 is a side section view of the trifurcation of the lead body of FIG. 1 illustrating a second aspect of the first embodiment of the present invention.

FIG. 5 illustrates the coupling of the trifurcation sleeve 28 with the proximal end of the lead body insulator 11 and the routing of the lead conductors 68, 84, 86 and 60 within the respective insulating layers 72, 86, and 90 and the tube 62 proximally into the insulating sleeves 31, 37, and 47 for direct or indirect attachment to the lead connector pins 34, 44, 50, and ring 38. In each case, it will be understood that the lead conductors 68, 84, 86 and 60 are coated with the conductive aerogel coatings or layers 69, 85, 89 and 66, respectively, through the trifurcation sleeve 28 and the insulating sleeves 31, 37, and 47.

The section view of FIG. 5 shows the stranded wire cable conductor 68 coated with the conductive aerogel layer 69 within the insulating coating 72 extending proximally out of lumen 78 of lead body insulator 74 through the lumen of spacer tube 124. The proximal end of the stranded wire conductor 68 is crimped into a closed end bore 136 of a conductive tubular coupling 128. The coiled wire conductor 60 within the insulating tube 62 extends into a lumen of a further insulating tube 122. The insulating tube 62 is adhered to the insulating tube 122, and the assembly extends proximally through a lumen of the tubular coupling 128, through the sleeve extension 37 and to the proximal connector assembly 36, where the coiled wire conductor 60 is coupled to the connector pin 44. The distal end of a coiled wire conductor 130 that extends proximally within the insulating sleeve 37 to the connector ring 38 is crimped to the tubular coupling 128 employing a crimping ring 132.

Proximal segments of the stranded wire cable conductors 84 and 88 coated with conductive aerogel layers 85 and 89, respectively, and over-coated with insulating layers 86 and 90, respectively, extend proximally from the lumens 76 and 80, respectively, through the lumens 138 and 140, respectively, and then through the respective insulating sleeves 31 and 47 to the respective lead connector pins 34 and 50 depicted in FIG. 1. The proximal segments of the stranded wire conductors 84 and 88 coated with conductive aerogel layers 85 and 89, respectively, and over-coated with insulating layers 86 and 90, respectively, extending through lumens 138 and 140, respectively, are preferably, but not necessarily, received within lumens of further insulating tubes 134 and 126, respectively.

The sleeve branch lumens 138 and 140 defined within trifurcation sleeve 28 are then typically backfilled with silicone rubber medical adhesive, providing a mechanical interconnection of all the components therein. The silicone rubber adhesive interconnection also assists in mechanically coupling the proximal end of the lead body insulator 74 to the trifurcation sleeve 28. As noted above, this fabrication results in a stiff and unyielding structure. In reference to FIG. 1, flexing of the trifurcation branches 33 and 49 in respective directions A and B can still occur and result in fracture of the stranded wire conductors 84 and 88 extending through the sleeve branch lumens 138 and 140.

In accordance with the present invention, the conductive aerogel coatings or layers 85 and 89 surrounding the stranded wire conductors 84 and 86 provide a deformable space that changes with the flexing and/or fracture of the stranded wire conductors 84 and 86. For example, fractures of the stranded wire conductors 84 and 86 can occur in the respective trifurcation branches 33 and 49 due to movement in the directions A and B of FIG. 1 during chronic implantation. It is expected that segments of the respective conductive aerogel layer or coating 85 and 89 will bend and stretch longitudinally or compress but remain intact to bridge any fracture that may occur. The conductive aerogel or coating 85, 89 adheres to itself like a sponge more than it adheres to the wire strand surfaces.

Figure 6:
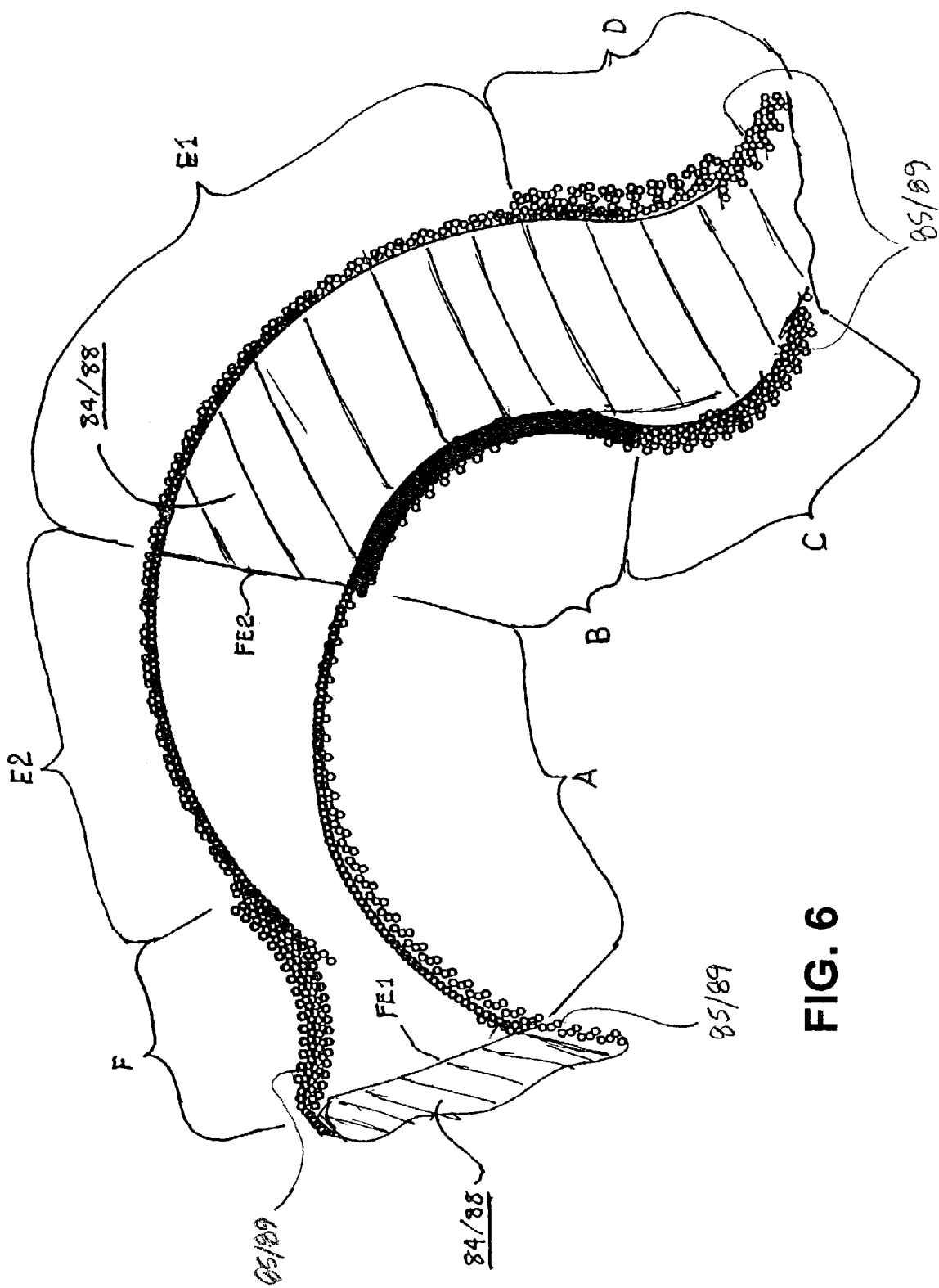
FIG. 6 is a schematic, cross-section, side view of a fracture in a segment of the stranded lead conductors of FIGS. 2, 4, and 5 and the bending, crushing and stretching of the conductive aerogel coating bridging the fracture.

Such deformation of the conductive aerogel layer or coating 85 and 89 surrounding one of the above-described stranded wire cable conductors 84 and 88 that fractures in response to movement or deformation of the respective trifurcation branches 33 and 49 in the respective directions A and B of FIG. 1 is schematically illustrated in FIG. 6. The stranded wire cable conductor 84 or 88 in respective trifurcation branch 33 or 49 has undergone bending forces that result in the wire fracturing leaving fractured ends FE1 and FE2 that have drawn apart, resulting in a gap between them as one or both of the fractured ends FE1 and FE2 tend to draw apart from one another. The overlying conductive aerogel layer or coating 85 or 89 can stretch longitudinally as the fractured ends FE1 and FE2 draw apart and leave the gap. The fractured end FE1 and/or end FE2 may or may not perforate through a side hole of the conductive aerogel layer or coating 85 or 89 and the non-conductive coating or coatings (not shown) overlying the respective conductive aerogel layer or coating 85 or 89. Despite the puncture, the remaining overlying conductive aerogel layer or coating 85 or 89 is expected to thin and stretch longitudinally to bridge the gap between the fractured ends FE1 and FE2 as shown in FIG. 6. The conductive aerogel layer or coating 85 or 89 is expected to bunch up and compress where a concave bend occurs and to stretch longitudinally where a convex bend occurs, which are shown in FIG. 6.

Through the concave bend "A", the conductive aerogel coating or layer 85 or 89 between the fractured ends FE1 and FE2 is effectively stretched somewhat and pushed into the gap by forces applied through or by the surrounding polymeric lead body, e.g., the medical adhesive filling the surrounding space as shown in FIG. 5. The conductive aerogel coating or layer 85 or 89 is not crushed since it can move into the gap between the fractured ends FE1 and FE2. But, the stranded wire cable conductor 84 or 88 prevents such movement in the convex bend "B", and so the conductive aerogel coating or layer 85 or 89 is crushed upon itself in that bend. In convex bend C, the conductive aerogel coating or layer 85 or 89 is not as severely crushed and tends to stretch away from the stranded wire cable conductor 84 or 88.

On the opposite side of the stranded wire cable conductor 84 or 88, the conductive aerogel coating or layer 85 or 89 tends to bunch and become thicker in the concave bend "D". The conductive aerogel coating or layer 85 or 89 tends to stretch longitudinally and outward away from the stranded wire cable conductor 84 or 88 in the convex bend segment E1 that encompasses the stranded wire cable conductor 84 or 88. The conductive aerogel coating or layer 85 or 89 tends to stretch longitudinally and become thinner in the in the convex bend segment E2 that bridges the gap until the curvature changes. The conductive aerogel coating or layer 85 or 89 tends to bunch and be pushed into the gap by forces applied through or by the surrounding polymeric lead body, e.g., the medical adhesive, in the concave bend F that extends along the gap to the fractured end F1.

Thus, the conductive aerogel is expected to maintain an electrical circuit bridging the gap between the fractured ends FE1 and FE2. It is expected that the conductive aerogel coatings would behave in a similar manner throughout the lead body and over both the illustrated straight and coiled wire conductors. Moreover, it is expected that the conductive aerogel coatings would behave in a similar manner when incorporated into the fabrication of lead bodies of the other types described above to cover or encase straight and coiled single and multi-filar wire conductors.

All patents and publications referenced herein are hereby incorporated by reference in their entireties; it will be understood that specifically described structures, functions and operations set forth in the above-referenced patents can be practiced in conjunction with the present invention, but they are not essential to its practice.

It will be understood that certain of the above-described structures, functions and operations of the above-described preferred embodiments are not necessary to practice the present invention and are included in the description simply for completeness of an exemplary embodiment or embodiments.

It is therefore to be understood, that within the scope of the appended claims, the invention may be practiced otherwise than as specifically described without actually departing from the spirit and scope of the present invention.

The invention claimed is:

1. An electrical medical lead comprising:
   an elongated, flexible and resilient, lead body extending from a proximal end to a distal end and including an insulative sheath and an elongated conductor, the insulative sheath including an elongated lumen and the elongated conductor extending through the lumen; and
   a layer of conductive aerogel within at least a portion of and extending for a distance along the elongated lumen in contact with the conductor, the layer of conductive aerogel deforming upon movement of the conductor within the lumen against the aerogel in response to applied stresses.

2. The electrical medical lead of claim 1, wherein the conductive aerogel comprises one of the group consisting of carbon, gold and platinum aerogels.

3. The electrical medical lead of claim 1, wherein the conductive aerogel provides a conductive pathway along the distance bridging any fracture of the conductor.

4. The electrical medical lead of claim 1, wherein the conductor comprises a substantially straight stranded wire conductor coated with a layer of conductive aerogel.

5. The electrical medical lead of claim 4, further comprising an insulating layer extending over the coated stranded wire conductor.

6. The electrical medical lead of claim 1, wherein the lead conductor comprises a coiled wire conductor coated with a layer of conductive aerogel.

7. The electrical medical lead of claim 6, further comprising an insulating layer extending over the coated coiled wire conductor.

8. An electrical medical lead comprising:
   an elongated, flexible and resilient, lead body extending from a proximal end to a distal end and including an insulative sheath and a plurality of elongated conductors, the insulative sheath including a plurality of elongated lumens and each of the plurality of elongated conductors extending through each of the plurality of lumens; and
   layers of conductive aerogel within at least a portion of and extending for a distance along each of the plurality of elongated lumens in contact with each of the plurality of conductors, the layers of conductive aerogel deforming upon lateral movement of each of the plurality of conductors within each of the plurality of lumens against the aerogel in response to applied stresses.

9. An electrical medical lead comprising:
   an elongated, flexible and resilient, lead body extending from a proximal end to a distal end and including an insulative sheath and a plurality of elongated conductors, the insulative sheath including a plurality of elongated lumens and each of the plurality of elongated conductors extending through each of the plurality of lumens;
   a sleeve including a trunk joined to the proximal end of the lead body and a plurality of branches extending proximally from the trunk; and
   a layer of conductive aerogel within at least a portion of the sleeve;
   wherein the plurality of elongated conductors extend through the sleeve trunk and each of the plurality of conductors further extends through each of the plurality of sleeve branches; and
   the layer of conductive aerogel is in contact with at least one of the plurality of conductors, the layer of aerogel deforming upon movement of the at least one conductor within the sleeve against the layer of conductive aerogel.

10. The electrical medical lead of claim 9, wherein the conductive aerogel comprises one of the group consisting of carbon, gold and platinum aerogels.

11. The electrical medical lead of claim 9, wherein the conductive aerogel provides a conductive pathway along the distance bridging any fracture of the lead conductor.

12. The electrical medical lead of claim 9, wherein at least one of the plurality of conductors comprises a substantially straight, stranded wire conductor coated with a layer of conductive aerogel.

13. The electrical medical lead of claim 12, further comprising an insulating layer extending over the coated stranded wire conductor.

14. The electrical medical lead of claim 9, wherein at least one of the plurality of conductors comprises a coiled wire conductor coated with a layer of conductive aerogel.

15. The electrical medical lead of claim 14, further comprising an insulating layer extending over the coated coiled wire conductor.

* * * * *